(12) United States Patent
Mako (10) Patent No.: US 10,786,221 B2
(45) Date of Patent: Sep. 29, 2020

(54) RADIATION IMAGING APPARATUS, RADIATION IMAGING SYSTEM, AND METHOD FOR CONTROLLING RADIATION IMAGING SYSTEM

(71) Applicant: CANON KABUSHIKI KAISHA, Tokyo (JP)

(72) Inventor: Yuta Mako, Fukuoka (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 38 days.

(21) Appl. No.: 16/267,527

(22) Filed: Feb. 5, 2019

(65) Prior Publication Data

US 2019/0247002 A1 Aug. 15, 2019

(30) Foreign Application Priority Data

Feb. 15, 2018 (JP) .................................. 2018-025353

(51) Int. Cl.
*A61B 6/00* (2006.01)
*H04N 7/56* (2006.01)
*G01T 1/17* (2006.01)
*H04N 5/32* (2006.01)

(52) U.S. Cl.
CPC ............ *A61B 6/548* (2013.01); *A61B 6/4233* (2013.01); *A61B 6/54* (2013.01); *A61B 6/563* (2013.01); *H04N 7/56* (2013.01); *G01T 1/17* (2013.01); *H04N 5/32* (2013.01)

(58) Field of Classification Search
None
See application file for complete search history.

(56) References Cited

U.S. PATENT DOCUMENTS

| 7,894,575 | B2 | 2/2011 | Tsubota et al. | |
|---|---|---|---|---|
| 10,162,067 | B2 | 12/2018 | Mako | |
| 2014/0254758 | A1* | 9/2014 | Saigusa | A61B 6/545 378/62 |
| 2016/0038114 | A1* | 2/2016 | Tajima | A61B 6/4283 378/62 |
| 2017/0350994 | A1 | 12/2017 | Yachi | |
| 2019/0290237 | A1* | 9/2019 | Kuwata | A61B 6/56 |

FOREIGN PATENT DOCUMENTS

| JP | 2002-052013 | 2/2002 |
|---|---|---|
| JP | 2010-081960 | 4/2010 |
| JP | 2014-147789 | 8/2014 |
| JP | 2017-164389 | 9/2017 |

* cited by examiner

*Primary Examiner* — Hoon K Song
(74) *Attorney, Agent, or Firm* — Venable LLP (57) ABSTRACT

A radiation imaging apparatus includes: a detection unit configured to detect emitted radiation and output radiation image data; a clock control unit that has an internal clock and is configured to control a timing at which the detection unit is driven, based on time information of the internal clock; and a communication unit configured to transmit and receive data through a network, wherein the communication unit, if a communication traffic of the radiation image data is at a threshold or less, transmits the time information to a control apparatus that is connected through the network, and the clock control unit corrects the time information of the internal clock using time information that is a reply from the control apparatus to the time information.

12 Claims, 7 Drawing Sheets

RADIATION IMAGING APPARATUS, RADIATION IMAGING SYSTEM, AND METHOD FOR CONTROLLING RADIATION IMAGING SYSTEM

BACKGROUND OF THE INVENTION

Field of the Invention

The present invention relates to a radiation imaging apparatus, a radiation imaging system, and a method for controlling a radiation imaging system,

Description of the Related Art

Conventionally, radiation imaging apparatuses and radiation imaging systems that digitize a radiation image obtained from radiation that is emitted from a radiation generating apparatus and has passed through a subject and perform image processing on the digitized radiation image to generate data of a clear radiation image have been commercialized.

In such a radiation imaging apparatus, in general, a two-dimensional solid-state image sensor is used in a radiation detector. The radiation detector operates by converting emitted radiation into a charge amount, accumulating charges in a capacitor, and repeating a readout and reset operation of the accumulated charge. With an image sensor that does not include an electronic shutter, when charges are read out or reset, if the image sensor is irradiated with radiation, charges that are irrelevant to radiation imaging are superimposed on a radiation image, and the quality of the radiation image decreases.

Thus, with a radiation imaging system, it is necessary to synchronize an operation timing of the radiation detector in the radiation imaging apparatus and an emission timing of the radiation generating apparatus.

Japanese Patent Laid-Open No. 2010-81960 discloses a radiation imaging system including a radiation source control apparatus having a first clock and a radiation imaging apparatus having a second clock that is synchronized with the first clock through communication of time information.

However, with the configuration disclosed in Japanese Patent Laid-Open No. 2010-81960, image data is transferred while a moving image is being captured, and thus time synchronization is not performed periodically in some cases. Also, even if time synchronization is performed, communication traffic for time synchronization at a timing is added to an end of communication traffic that is being buffered at this point in time, thus processing for time synchronization is delayed, and a time lag is likely to occur between the radiation source control apparatus and the radiation imaging apparatus.

The present invention provides a radiation imaging technique capable of performing time synchronization with higher accuracy, even in a case where image data is transferred while a moving image is being captured.

SUMMARY OF THE INVENTION

According to one aspect of the present invention, there is provided a radiation imaging apparatus comprising: a detection unit configured to detect emitted radiation and output radiation image data; a clock control unit that has an internal clock and is configured to control a timing at which the detection unit is driven, based on time information of the internal clock; and a communication unit configured to transmit and receive data through a network, wherein the communication unit, if a communication traffic of the radiation image data is at a threshold or less, transmits the time information to a control apparatus that is connected through the network, and the clock control unit corrects the time information of the internal clock using time information that is a reply from the control apparatus to the time information.

According to another aspect of the present invention, there is provided a radiation imaging system comprising a radiation imaging apparatus and a control apparatus configured to control the radiation imaging apparatus, wherein the radiation imaging apparatus comprises: a detection unit configured to detect emitted radiation and output radiation image data; a clock control unit that has an internal clock and is configured to control a timing at which the detection unit is driven, based on time information of the internal clock; and a communication unit configured to transmit and receive data through a network, wherein the communication unit, if a communication traffic of the radiation image data is at a threshold or less, transmits the time information to the control apparatus that is connected through the network, and the clock control unit corrects the time information of the internal clock using time information that is a reply from the control apparatus to the time information.

According to still another aspect of the present invention, there is provided a method for controlling a radiation imaging system including a radiation imaging apparatus and a control apparatus configured to control the radiation imaging apparatus, the method comprising: detecting emitted radiation and outputting radiation image data using a detection unit; controlling, in a clock control unit that has an internal clock, a timing at which the detection unit is driven, based on time information of the internal clock; if a communication traffic of the radiation image data is at a threshold or less, a communication unit transmitting the time information to the control apparatus that is connected through a network, and correcting the time information of the internal clock using time information that is a reply from the control apparatus to the time information.

According to the present invention, it is possible to provide a radiation imaging technique capable of performing time synchronization with higher accuracy.

Further features of the present invention will become apparent from the following description of exemplary embodiments with reference to the attached drawings.

DESCRIPTION OF THE EMBODIMENTS

Hereinafter, exemplary embodiments of the present invention will be described in detail with reference to the drawings. However, the constituent elements described in this embodiment are merely examples, and are not limited by the following individual embodiments. Note that radiation includes α rays, β rays, γ rays, and various particle rays, in addition to X-rays.

First Embodiment

Figure 1:
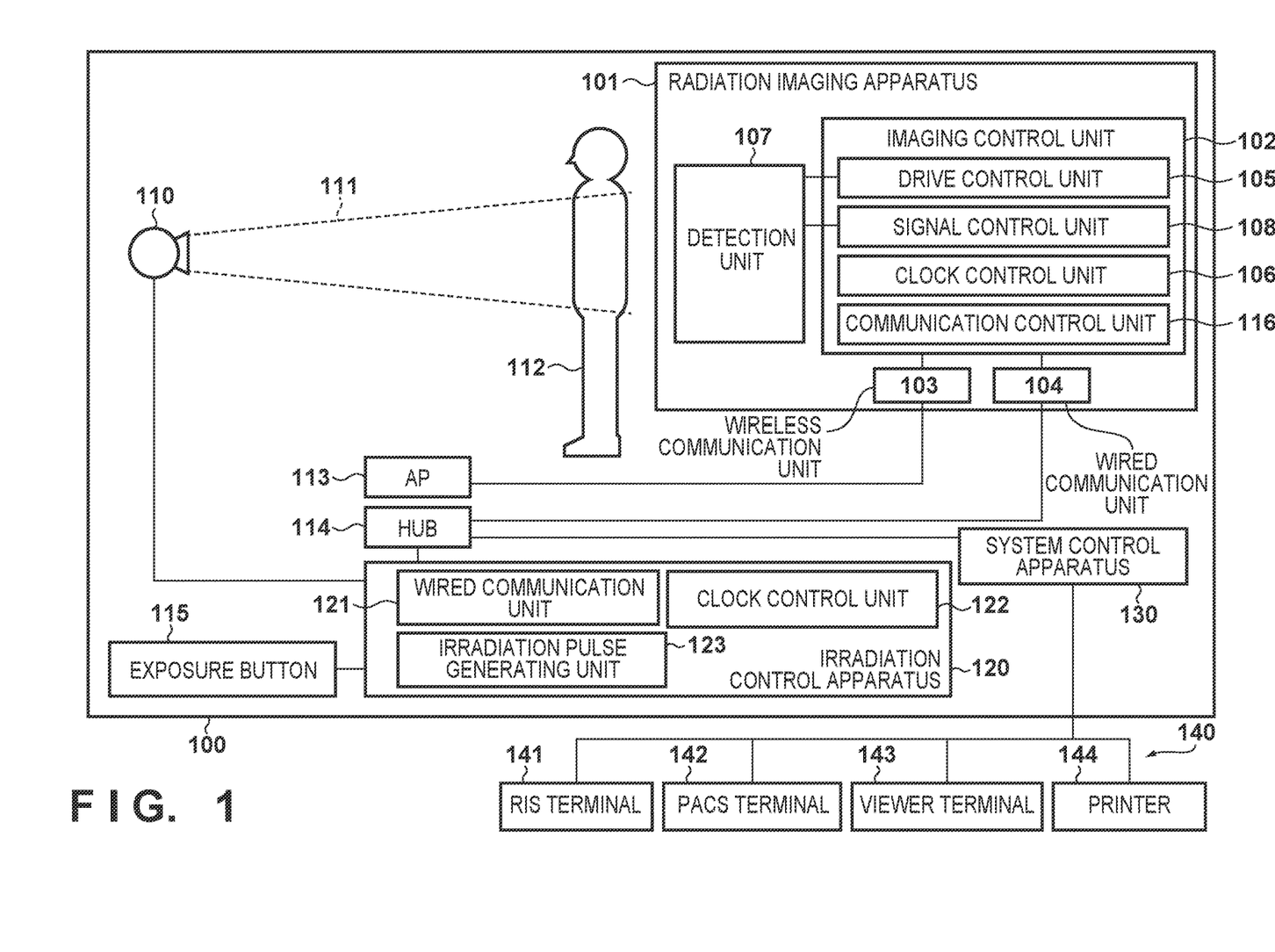
FIG. 1 is a diagram showing a configuration example of a radiation imaging system according to an embodiment.

FIG. 1 is a diagram showing a configuration example of a radiation imaging system 100 according to an embodiment of the present invention. A radiation imaging system 100 according to the present embodiment includes a radiation generating apparatus 110 configured to emit radiation, an irradiation control apparatus 120 configured to control radiation emitted by the radiation generating apparatus 110, a radiation imaging apparatus 101 that has a detection unit 107 configured to detect emitted radiation and output radiation image data, and a system control apparatus 130 configured to control overall operation of the radiation imaging system 100.

Herein, the radiation imaging apparatus 101 includes a clock control unit 106 configured to control timing for driving the detection unit 107 based on time information of an internal clock, and communication units (a wireless communication unit 103, a wired communication unit 104, and a network interface 304) configured to transmit and receive data via a network. If the communication traffic (also referred to as a communication interval such as a gap time period or a communication load) of the radiation image data is at a threshold or less, the communication units transmit time information (for example, a time synchronization packet) to the irradiation control apparatus 120 that is connected via the network, and the clock control unit 106 corrects time information of the internal clock using the time information that is a reply from the irradiation control apparatus 120 to the time information.

In the present embodiment, the radiation imaging apparatus 101 determines whether or not the communication traffic of the radiation image data in the communication units is at a threshold or less, based on an image communication schedule. For example, the radiation imaging apparatus 101 determines whether a gap time period in which a time synchronization packet can be transmitted to a transmission buffer is present from when communication of the image data packet ends to when communication of the next image data packet starts, based on the image communication schedule, and generates the time synchronization packet based on the determination result. If the gap time period is present, the radiation imaging apparatus 101 generates the time synchronization packet based on the result of the determination. Hereinafter, a specific configuration of an embodiment will be described.

In the radiation imaging system 100, the radiation imaging apparatus 101, the irradiation control apparatus 120, and the system control apparatus 130 are connected to each other via a wireless or wired communication network, and are capable of transmitting and receiving information between each other. The communication network includes a wireless LAN access point (AP) 113 and a hub (HUB) 114, and information is configured to be capable of being transmitted and received in the form of a message between apparatuses that are connected via the communication network.

The radiation imaging apparatus 101, the irradiation control apparatus 120, and the system control apparatus 130 determine connection states between each other, and are configured to be capable of automatically switching to wired communication when a wired connection is established. Note that, although a configuration that allows communication using both a wireless communication method and a wired communication method was described as the configuration of the radiation imaging system 100, the configuration of the radiation imaging system 100 is not limited thereto, and a system can be constructed using either one of the communication methods.

In contrast, the radiation generating apparatus 110 and the irradiation control apparatus 120 are electrically directly connected to each other without using the communication network, and thus information is not converted into the form of a message, but instead information is directly transmitted as an electrical signal between the radiation generating apparatus 110 and the irradiation control apparatus 120. Note that, although an electrical direct connection is highly reliable and thus is favorably used, the radiation generating apparatus 110 and the irradiation control apparatus 120 can be connected using a communication network.

Herein, the radiation generating apparatus 110 is an apparatus configured to irradiate a subject 112 with radiation based on irradiation control performed by the irradiation control apparatus 120. The radiation generating apparatus 110 has a tube bulb and a diaphragm mechanism for emitting radiation. The radiation generating apparatus 110 is controlled by the irradiation control apparatus 120, and emits pulsed or continuous radiation 111 at a predetermined tube voltage and a predetermined tube current using signals (irradiation control signals) from the irradiation control apparatus 120. The radiation 111 emitted from the radiation generating apparatus 110 is imaged by the radiation imaging apparatus 101 synchronized with an irradiation timing.

The radiation imaging apparatus 101 is an apparatus configured to perform radiation imaging based on radiation that has passed through the subject 112 and acquire a radiation image that is the captured image. The radiation imaging apparatus 101 includes the detection unit 107 in which pixels that convert radiation into electrical signals are arranged two-dimensionally and an imaging control unit 102.

The detection unit 107 has a configuration in which pixels that each include a switch element such as a TFT and a photoelectric converting element are arranged two-dimensionally (for example, a two-dimensional array form), and phosphors configured to convert radiation into visible light are provided on each photoelectric converting element, for example. The radiation incident on the detection unit 107 is converted into visible light by the phosphors, the converted visible light is incident on a photoelectric converting element of each pixel, and charges (electrical signal) that correspond to the visible light are generated as pieces of radiation image data in each photoelectric converting element.

The imaging control unit 102 performs processes related to driving and controlling the detection unit 107, various image processes on data of a captured radiation image, saving of radiation image data, determination of a timing at which radiation image data is transferred, transfer and control of radiation image data, and the like.

The imaging control unit 102 includes a drive control unit 105, a clock control unit 106, a signal control unit 108, and a communication control unit 116. The drive control unit 105 drives and controls the detection unit 107. The clock control unit 106 holds an internal clock, corrects the time of the internal clock according to the irradiation control apparatus 120, and controls a timing at which the detection unit 107 is driven based on time information of the internal clock.

The signal control unit 108 performs various image processes on the radiation image data acquired from the detection unit 107, and processes related to saving of radiation image data, determination of a timing at which radiation image data is transferred, transfer and control of radiation image data, and the like. The communication control unit 116 is connected to the wireless communication unit 103 and the wired communication unit 104 and controls communication of each communication unit.

The radiation image data that is processed by the imaging control unit 102 is transferred to the system control apparatus 130, and is subjected to image processing in the system control apparatus 130. The system control apparatus 130 transmits and receives a signal under the communication control of the communication control unit 116 using the wireless communication unit 103 or the wired communication unit 104. Also, there are cases where signals are transmitted and received with the radiation imaging apparatus 101 directly connected to the system control apparatus 130, and the system control apparatus 130 directly connected to the irradiation control apparatus 120.

An operator can set conditions required for performing imaging using an operation apparatus and a display device (not shown) that are connected to the system control apparatus 130, and the operation apparatus is capable of outputting information for emitting radiation. The irradiation control apparatus 120 controls radiation emitted by the radiation generating apparatus 110. The information output from the operation apparatus is processed by the irradiation control apparatus 120, and the radiation generating apparatus 110 emits radiation based on the control of the irradiation control apparatus 120 due to an exposure button 115 being pressed down. The exposure button 115 is used to control an irradiation timing or an irradiation period of still image capturing or fluoroscopic imaging.

The irradiation control apparatus 120 is controlled based on a signal that is input from the exposure button 115 or a signal that is input from the system control apparatus 130 via a wired communication unit 121. The irradiation control apparatus 120 has the wired communication unit 121, a clock control unit 122, and an irradiation pulse generating unit 123.

The clock control unit 122 of the irradiation control apparatus 120 holds time information, and the time information is used for synchronously controlling the timing at which the detection unit 107 of the radiation imaging apparatus 101 is driven and the timing at which radiation is emitted from the radiation generating apparatus 110. The irradiation pulse generating unit 123 generates a signal for controlling the radiation emission timing (irradiation control signal) based on the time information of the clock control unit 122, and outputs the generated signal to the radiation generating apparatus 110.

The system control apparatus 130 is an apparatus that is configured to control the overall operation of the radiation imaging system 100, and is capable of performing image processing on radiation image data, performing control related to collecting and displaying captured images, accepting an imaging order, and registering imaging information.

The system control apparatus 130 is connected to a network 140 constituted by a LAN (Local Area Network) and the like, for example. Also, an RIS (Radiology Information System) 141 (RIS terminal) that is a radiation information system, a PACS (Picture Archiving and Communication Systems) 142 (PACS terminal) that is an image storage communication system, a viewer terminal 143, and a printer 144 are connected to the network 140.

Mutual communication between the system control apparatus 130 and the RIS terminal 141 and the PACS terminal 142 is possible via the network 140, and it is possible to exchange an order to capture a radiation image, imaging information including patient information (subject information), and captured image data.

The RIS terminal 141 is an operation terminal connected to the radiation imaging system 100, and constitutes an information system in a radiology department. This information system is an information management system that collectively manages information added to a radiation image or an inspection order, for example. The additional information includes inspection information including an inspection ID or a reception number. The operator can input the inspection order (inspection instruction) via the RIS terminal 141, and perform imaging using the radiation imaging system 100 in accordance with this inspection order. In the present embodiment, the input inspection order is stored in and managed by the RIS terminal 141, but may also be stored in and managed by a server (not shown) connected to the RIS terminal 141 and the radiation imaging system 100. Note that the input inspection order may also be stored in and managed by the radiation imaging system 100.

The PACS terminal 142 stores and manages the image captured by the radiation imaging system 100. That is, the PACS terminal 142 functions as a portion of an image management system configured to manage the captured image. The viewer terminal 143 is capable of displaying and outputting a radiation image stored in the PACS terminal 142. The printer 144 is capable of outputting the radiation image stored in the PACS terminal 142 to a medium such as a film. The operator captures a radiation image using the radiation imaging system 100 based on the inspection order including a plurality of pieces of inspection information that were input via the RIS terminal 141.

The inspection information includes imaging protocol information. An imaging protocol includes parameter information or imaging execution information that is used in imaging or image processing, and imaging environmental information such as the type of sensor or an imaging orientation.

The radiation imaging system 100 supports capturing of at least one of a radiation still image and a radiation moving image, and in particular, parameters such as a frame rate and the length of a radiation pulse per frame are set to the imaging protocol for imaging the moving image. Also, the inspection information includes information for specifying the inspection ID and the inspection order such as the reception number and information for specifying a radiation image corresponding to the inspection order.

When radiation imaging is performed, upon the exposure button 115 being pressed down at a timing at which the operator desires to carry out imaging, a request for radiation emission is transmitted to the irradiation control apparatus 120 as an electrical signal. When the exposure button 115 is pressed down, the irradiation control apparatus 120 generates a message to start imaging, and, in an exchange, provides the message to the radiation imaging apparatus 101 via a communication network. After messages have been exchanged, the irradiation pulse generating unit 123 of the irradiation control apparatus 120 generates a signal (irradiation control signal) for controlling the timing of radiation emission based on the time information of the clock control unit 122, and outputs the generated signal to the radiation generating apparatus 110. The radiation generating apparatus 110 emits the radiation 111 based on the signal (irradiation control signal) output from the irradiation pulse generating unit 123.

On the other hand, in the radiation imaging apparatus 101, after messages have been exchanged with the irradiation control apparatus 120, the drive control unit 105 generates a drive control signal for driving the detection unit 107 and acquires the radiation image data generated by the detection unit 107. The clock control unit 106 in the radiation imaging apparatus 101 holds the time information, and the drive control unit 105 generates the drive control signal based on the time information of the clock control unit 106. The drive control unit 105 controls generation of the drive control signal so as to acquire radiation image data at a time when the drive control signal does not overlap with the irradiation control signal for controlling radiation emission. That is, the acquisition of the radiation image data is controlled in a time span that is different from the time span of radiation emission.

When the operator of the radiation imaging system stops pressing down the irradiation button in order to stop imaging, the irradiation pulse generating unit 123 of the irradiation control apparatus 120 stops generating the irradiation control signal, generates a message to stop imaging, and, in an exchange, provides the message to the radiation imaging apparatus 101. After messages have been exchanged with the irradiation control apparatus 120, in the radiation imaging apparatus 101, the drive control unit 105 stops acquisition of the radiation image data from the detection unit 107.

In the above-described synchronous operation, the radiation image data is acquired in a time span that is different from the time span of radiation emission. In order to realize this synchronous operation, it is necessary to set times that are accurately synchronized to the clock control unit 122 in the irradiation control apparatus 120 and the clock control unit 106 in the radiation imaging apparatus 101.

Figure 2:
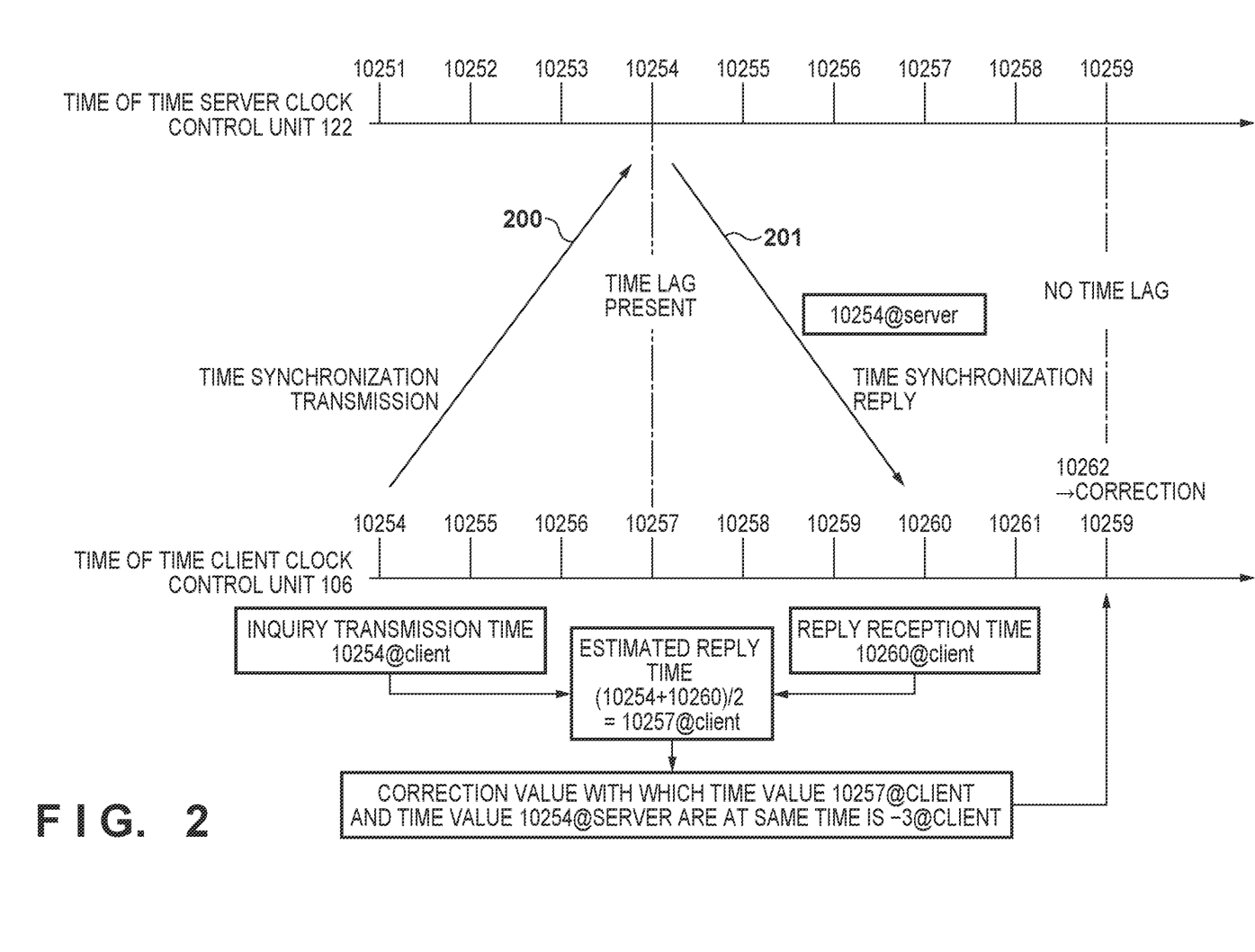
FIG. 2 is a diagram illustrating a procedure for synchronizing time information between apparatuses according to an embodiment.

FIG. 2 is a diagram illustrating the procedure for synchronizing the time information of the clock control unit 106 in the radiation imaging apparatus 101 with the time information of the clock control unit 122 in the irradiation control apparatus 120. For example, the clock control unit 122 in the irradiation control apparatus 120 is capable of operating as a time server, and if the clock control unit 122 operates as a time server, the time information of the clock control unit 122 serves as the reference time in the radiation imaging system. Also, it is presumed that the clock control unit 106 in the radiation imaging apparatus 101 is capable of operating as a time client, and the clock control unit 106 operates following the time server.

First, the radiation imaging apparatus 101 transmits a time synchronization transmission message (time synchronization transmission information 200) to the clock control unit 122 of the irradiation control apparatus 120 through the wired communication unit 104 or the wireless communication unit 103.

At this time, when the clock control unit 106 of the radiation imaging apparatus 101 transmits the time synchronization transmission information 200, the clock control unit 106 stores the time information of the clock control unit 106 at the transmission time in the clock control unit 106 and then transmits the time synchronization transmission information 200. For example, if the clock control unit 106 transmits the time synchronization transmission information 200 at a time value 10254 indicated by the clock held by the clock control unit 106, the clock control unit 106 stores the time value 10254 in an internal memory as an inquiry transmission time, and transmits the time synchronization transmission message (time synchronization transmission information 200).

The irradiation control apparatus 120 that has received a time synchronization transmission message (time synchronization transmission information 200) from the clock control unit 106 of the radiation imaging apparatus 101 transmits a time synchronization reply message (time synchronization reply information 201). That is, similarly to the time client, the clock control unit 122 of the irradiation control apparatus 120 transmits the time synchronization reply message (time synchronization reply information 201) through the wired communication unit 121, the hub (HUB) 114, or the wireless LAN access point (AP) 113.

For example, when transmitting the time synchronization reply information 201 at the time value 10254 indicated by the clock held by the clock control unit 122, the clock control unit 122 stores the time value 10254 as a reply transmission time in the time synchronization reply information 201 (10254@server, "@server" indicates the time in a time server hereinafter) and transmits the time value 10254.

The radiation imaging apparatus 101 receives the time synchronization reply message (time synchronization reply information 201) transmitted from the irradiation control apparatus 120. At this time, the reply message (time synchronization reply information 201) is acquired at a pre-correction time of the clock control unit 106 of the radiation imaging apparatus 101 (reply reception time). For example, in FIG. 2, the clock control unit 106 acquires the time synchronization reply information 201 at a time value 10260, and stores the acquired time synchronization reply information 201 in the internal memory as the reply reception time.

If communication time periods (travel time periods) required for communication of both messages of the time synchronization transmission information 200 and the time synchronization reply information 201 are equal to each other and a time when the irradiation control apparatus 120 transmits the time synchronization reply information 201 (estimated reply time) is estimated based on the time of the clock held by the clock control unit 106, the estimated relay time can be estimated as the intermediate time between the inquiry transmission time 10254 (10254@client, and "@client" indicates the time in the client hereinafter) and the reply reception time 10260 (10260@client).

That is, the clock control unit 106 is capable of estimating the estimated reply time through the average calculation (10254+10260)/2=10257 (10257@client).

In order to obtain a time lag between the radiation imaging apparatus 101 and the irradiation control apparatus 120, the clock control unit 106 (client) acquires a difference between the estimated reply time in the client and the reply transmission time in the irradiation control apparatus 120 (time server). That is, when the clock control unit 106 acquires a difference time (time difference) between the estimated reply time (10257@client) and the reply transmission time (10254@server), it can be seen that there is a time lag between the estimated reply time and the reply transmission time, and the time of the radiation imaging apparatus 101 advances by 10257−10254=3. A correction value with which the time value 10257@client and the time value 10254@server are at the same time is −3@client.

The clock control unit 106 corrects the time value of the clock of the clock control unit 106 based on the acquired time difference, and synchronizes the corrected time value of the clock control unit 106 with the time of the clock control unit 122.

The clock control unit 106 corrects the time value by subtracting the difference time (time difference) from the time information of the clock control unit 106 of the client such that the estimated reply time 10257 (10257@client) of the client and the reply transmission time 10254 (10254@server) of the time server are at the same time.

That is, the clock control unit 106 corrects the time value of the clock by subtracting a correction value (−3@client) from the time value (10262@client) of the clock control unit 106. The corrected time value becomes the time value (10259@client) in FIG. 2, and this time value is the same as the time value (10259@server) of the clock of the clock control unit 122.

It is possible to calculate the time difference between the clock control unit 106 and the clock control unit 122 through the above-described calculation processing, and the clock control unit 106 corrects the time information of the clock control unit 106 based on the calculated time difference. Accordingly, the radiation imaging apparatus 101 and the irradiation control apparatus 120 enter a no-time-lag state (time synchronization state).

Although the example shown in FIG. 2 is described assuming that the clock control unit 122 in the irradiation control apparatus 120 serves as the time server and the clock control unit 106 in the radiation imaging apparatus 101 serves as the time client, the time server and the time client may be switched. For example, the clock control unit 122 may function as the time client, and the clock control unit 106 may function as the time server.

Also, although the estimated reply time is acquired based on one inquiry in which the time synchronization transmission information 200 and the time synchronization reply information 201 are combined into one set and the correction value for the time (time synchronization correction value) is determined from the difference time (time difference) between the estimated reply time and the inquiry transmission time in the example shown in FIG. 2, actually, fluctuations may occur in a communication time period (travel time period), and thus the correction value for the time based on a single inquiry may deviate from the true time.

In particular, while a moving image is being captured, the transfer of image data occupies the network interface, and thus transmission of a time synchronization packet may be delayed. Thus, if the time synchronization packet is delayed and a standby state arises in the transmission buffer, a case may develop where an accurate time difference cannot be calculated and there is a difference in time between the clock control unit 106 and the clock control unit 122. Thus, it is also possible to calculate the correction value for the time by making an inquiry a plurality of times and statistically processing the time difference acquired in correspondence with each inquiry.

In the radiation imaging system according to the present embodiment, various pieces of information such as the captured radiation image data, a message that is exchanged for controlling starting and ending of imaging, an inquiry and a reply for synchronizing the times, and the like are transmitted through the network. In addition to these, a command to transmit pre-setting information, a message to report an abnormality or normality of each apparatus, and the like are included. These pieces of information are transmitted and received from the wired communication unit 104 or the wireless communication unit 103 in the radiation imaging apparatus 101. These pieces of information transmitted through the network pass through the same medium, but in different manners of data communication (transfer). For example, the radiation image data is constructed by a large amount of data, compared to the time synchronization packet, and is thus split into and transmitted as multiple image data packets.

Also, a gap period (time period), which is a communication interval, is provided from when the transfer of one image (image data packets) ends to when the next image (image data packets) is transferred. Even if image transfer processing is delayed, it does not matter as long as this gap period (time period) is not lost. On the other hand, although communication of the time synchronization packet for synchronizing the times is constituted by a small number of packets, the delay of the time synchronization packet leads to a time difference estimation error between clocks of the radiation imaging apparatus 101 and the irradiation control apparatus 120, and thus it is preferable to transmit and receive packets without a delay.

In the present embodiment, if the transmission buffer includes a large amount of data such as in the case of transfer of image data, the timing of the time synchronization packet communication is controlled by checking an image communication schedule for the image data packets in advance such that the time synchronization packets do not remain in the transmission buffer.

Figure 3:
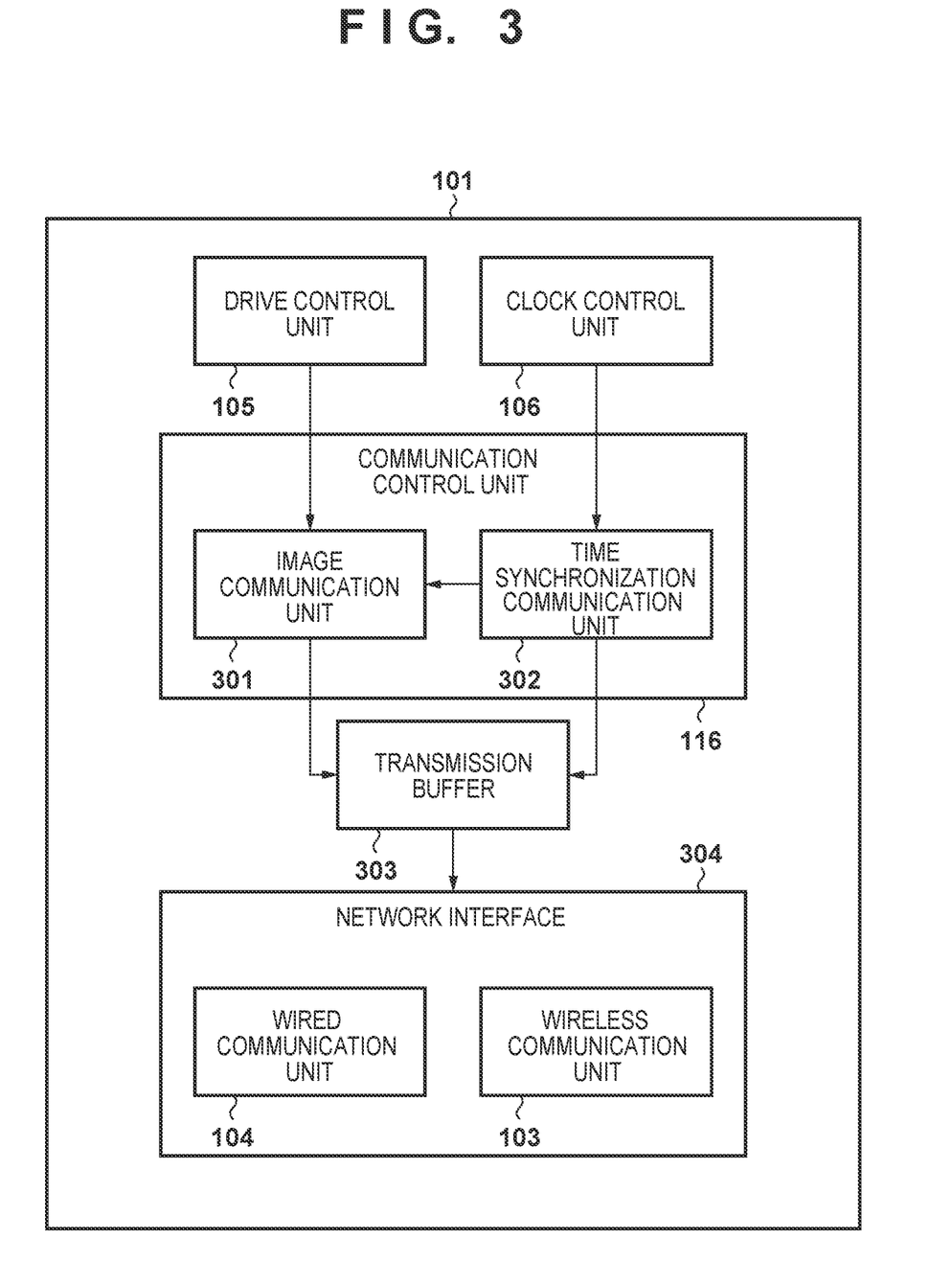
FIG. 3 is a diagram illustrating communication processing in a radiation imaging apparatus of a first embodiment.

Hereinafter, time synchronization packet transmission processing according to the present embodiment will be described with reference to FIGS. 3 to 5. FIG. 3 is a block diagram illustrating communication processing in the radiation imaging apparatus 101 in the first embodiment. In the following description, the wired communication unit 104 and the wireless communication unit 103 are collectively referred to as a network interface 304.

The communication control unit 116 includes an image communication unit 301 and a time synchronization communication unit 302. The image communication unit 301 acquires image data from the drive control unit 105, performs processing for generating packets (image data packet generation) and the like, and transmits the generated packets to the transmission buffer 303.

The time synchronization communication unit 302 acquires time information from the clock control unit 106, performs processing for generating packets (time synchronization packet generation) and the like, and transmits the generated packets to a transmission buffer 303. The transmission buffer 303 temporarily stores packets received from the communication control unit 116, and transmits the packets to the network interface 304.

Figure 4:
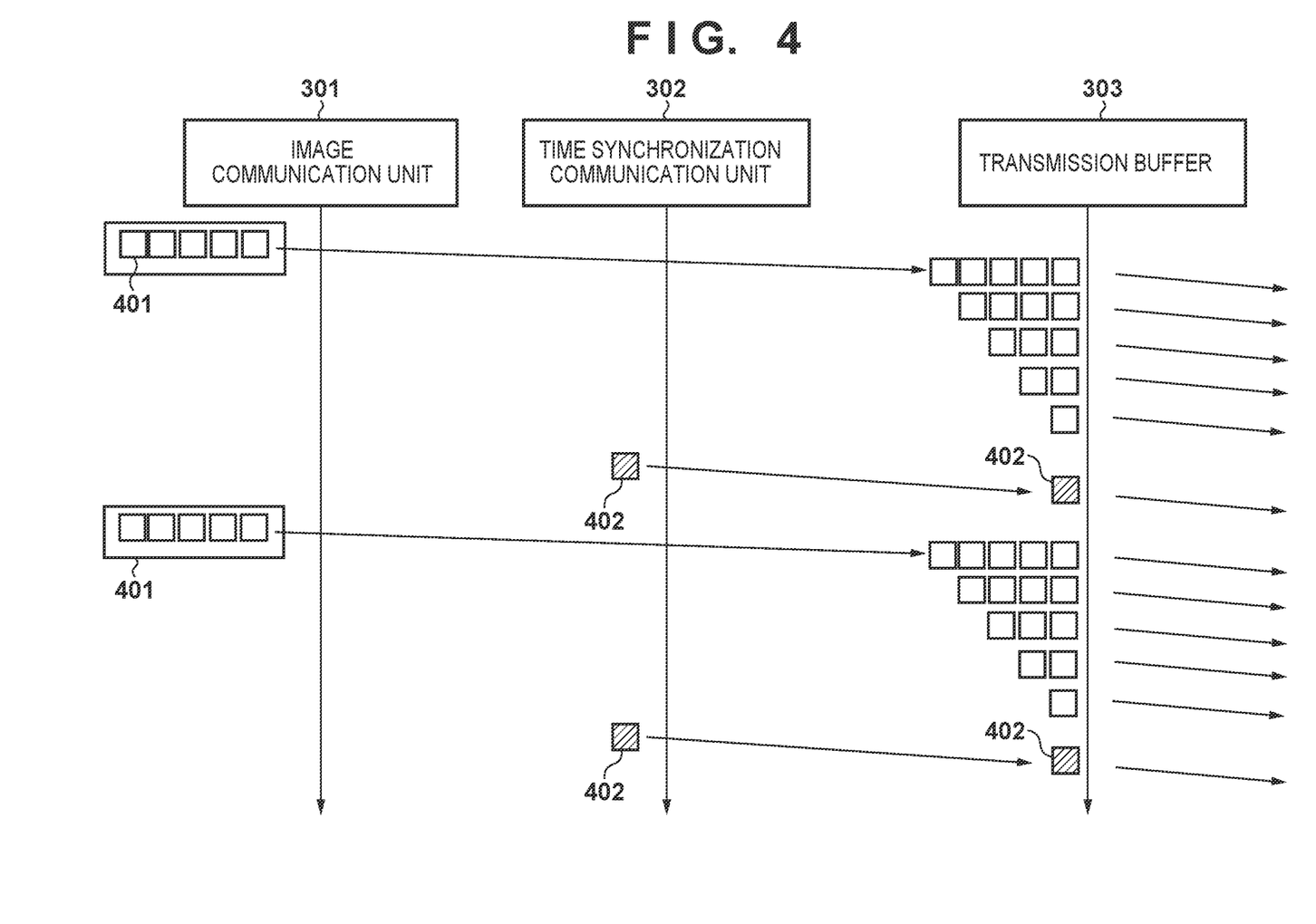
FIG. 4 is a diagram that schematically shows transmission of packets to a transmission buffer from an image communication unit and time synchronization communication unit.

FIG. 4 is a diagram schematically showing the transmission of packets from the image communication unit 301 and the time synchronization communication unit 302 to the transmission buffer 303. The time synchronization communication unit 302 makes an inquiry about when the image data packets are to be communicated to the image communication unit 301, in advance. The time synchronization communication unit 302 acquires information on the image communication schedule related to a timing for starting communication and ending communication in response to the inquiry. Herein, the information on the image communication schedule includes information related to a time period (gap time period) from the end of communication of a given image data packet to the start of communication of the next image data packet.

The image communication unit 301 transfers an image data packet 401 to the transmission buffer 303, and the transmission buffer 303 stores the image data packet 401 and successively transmits the image data packet 401 to the network interface 304.

The time synchronization communication unit 302 transmits a time synchronization packet 402 to the transmission buffer 303 in the gap time period immediately after the transfer of the image data packet 401 from the image communication unit 301 to the transmission buffer 303 ends, based on the timing at which the transmission of the image data packet 401 acquired from the image communication unit 301 in response to the inquiry ends.

The time synchronization communication unit 302 periodically makes an inquiry to the image communication unit 301, and if there is a gap time period in which the time synchronization packet 402 can be transmitted by the time synchronization communication unit 302 to the transmission buffer 303, the time synchronization communication unit 302 generates the time synchronization packet 402 and transfers the generated time synchronization packet 402 to the transmission buffer 303.

With a time synchronization packet communication method according to the present embodiment, a time synchronization packet communication timing is controlled such that overlapping between a time synchronization packet transmission timing and the image data packet communication period is avoided in advance, and a time synchronization packet is prevented from remaining in the transmission buffer and being delayed.

Figure 5:
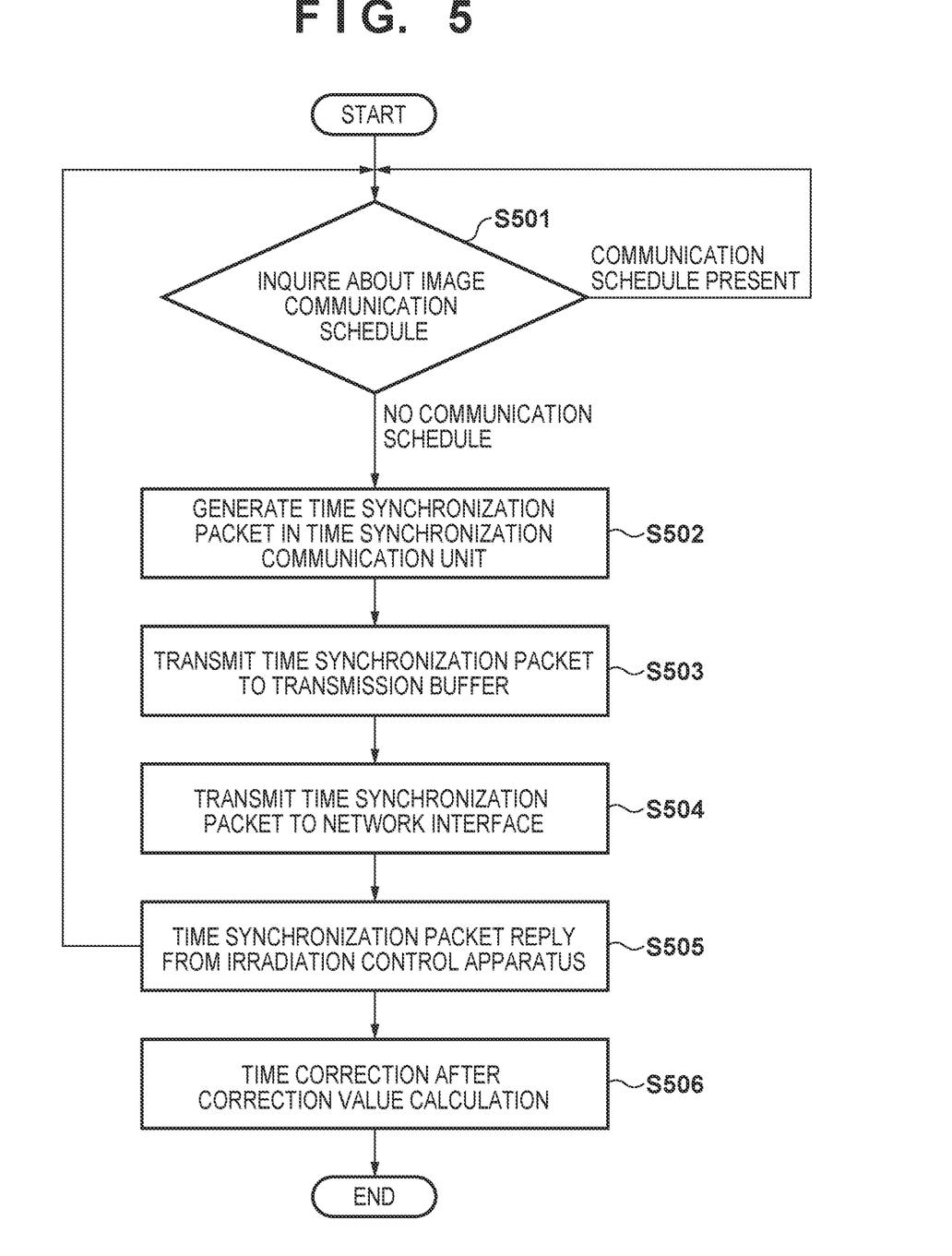
FIG. 5 is a diagram illustrating the flow of processing for transmitting a time synchronization packet in the first embodiment.

FIG. 5 is a diagram illustrating the flow of time synchronization packet transmission processing in the first embodiment.

In step S501, upon receiving a time synchronization start signal from the clock control unit 106, the time synchronization communication unit 302 makes an inquiry about the image communication schedule to the image communication unit 301. The time synchronization communication unit 302 determines, based on the image communication schedule, whether a time period from the end of communication of a given image data packet to the start of communication of the next image data packet includes a gap time period in which the time synchronization packet 402 can be transmitted to the transmission buffer 303, and controls generation of the time synchronization packet 402 based on the result of the determination. If the time period does not include the gap time period, the processing returns to step S501, the time synchronization communication unit 302 makes an inquiry about the image communication schedule and determines whether or not the time period includes a gap time period. That is, the time synchronization communication unit 302 periodically checks the image communication schedule, and makes inquiries until the image communication schedule includes a gap time period in which the time synchronization packet can be transmitted.

In the determination in step S501, if the image communication schedule includes a gap time period, the time synchronization communication unit 302 generates the time synchronization packet 402 in step S502, and the processing proceeds to step S503. In step S503, the time synchronization communication unit 302 transmits the time synchronization packet 402 to the transmission buffer 303.

In step S504, the transmission buffer 303 stores the time synchronization packet 402, and transmits the time synchronization packet 402 to the network interface 304. Then, the time synchronization packet 402 (time synchronization transmission information 200 (FIG. 2)) is transmitted from the network interface 304 to the irradiation control apparatus 120. When the time synchronization packet 402 is transmitted, the time when the time synchronization packet 402 is transmitted is stored in the radiation imaging apparatus 101 as an inquiry transmission time (FIG. 2).

In step S505, the irradiation control apparatus 120 makes a reply to the time synchronization packet 402 (time synchronization transmission information 200). The irradiation control apparatus 120 that has received the time synchronization transmission information 200 transmits a time synchronization reply message (time synchronization reply information 201) to the radiation imaging apparatus 101.

In step S506, the clock control unit 106 of the radiation imaging apparatus 101 calculates the correction value and performs time correction.

The radiation imaging apparatus 101 performs time average calculation based on a time when the time synchronization reply message (time synchronization reply information 201) transmitted from the irradiation control apparatus 120 is received (reply reception time) and the inquiry transmission time stored in step S504, and acquires an estimated reply time.

Then, the time information of the clock control unit 106 is corrected based on a time difference calculated using a difference between the estimated reply time in the clock control unit 106 of the radiation imaging apparatus 101 and the reply transmission time stored in the reply message (time synchronization reply information 201). Accordingly, the radiation imaging apparatus 101 and the irradiation control apparatus 120 enter a no-time-lag state (time synchronization state).

Note that it is also possible to calculate a correction value for a time by repeating the processing flow from step S501 to step S505 a plurality of times so as to statistically process the time difference acquired through a plurality of instances of processing.

According to the present embodiment, the time synchronization communication unit 302 is capable of controlling a time synchronization packet communication timing based on the image communication schedule of the image communication unit 301 such that overlapping between the time synchronization packet transmission timing and the image data packet communication period is avoided. Accordingly, it is possible to prevent the time synchronization packet from remaining in the transmission buffer and being delayed.

According to the present embodiment, it is possible to provide a radiation imaging technique capable of easily performing time synchronization with higher accuracy and performing radiation imaging. Even if image data is transferred while a moving image is being captured, a time synchronization packet communication timing is controlled so as to avoid overlapping with an image data packet communication period, and an error in the time information is corrected between the radiation imaging apparatus 101 and the irradiation control apparatus 120, and thus it is possible to easily perform time synchronization with higher accuracy and perform radiation imaging under highly accurate time synchronization.

Second Embodiment

In the first embodiment, as a result of the time synchronization communication unit 302 checking the image communication schedule of the image communication unit 301, a time synchronization packet communication timing is controlled such that overlapping between a time synchronization packet transmission timing and the image data packet communication period is avoided.

In the present embodiment, a configuration will be described in which a radiation imaging apparatus 101 notifies a time synchronization communication unit 302 as to whether or not communication traffic of radiation image data in a communication unit is at a threshold or less and about the state of an image data packet stored in a transmission buffer 303.

For example, in the radiation imaging apparatus 101, if the image data packet is stored in the transmission buffer 303 for storing data, the communication unit determines that the communication traffic exceeds the threshold, and the radiation imaging apparatus 101 does not generate time information (time synchronization packet). On the other hand, if the image data packet is not stored in the transmission buffer 303, the communication unit determines that the communication traffic is at the threshold or less, and the radiation imaging apparatus 101 generates time information (time synchronization packet). Hereinafter, a specific configuration of the embodiment will be described.

Figure 6:
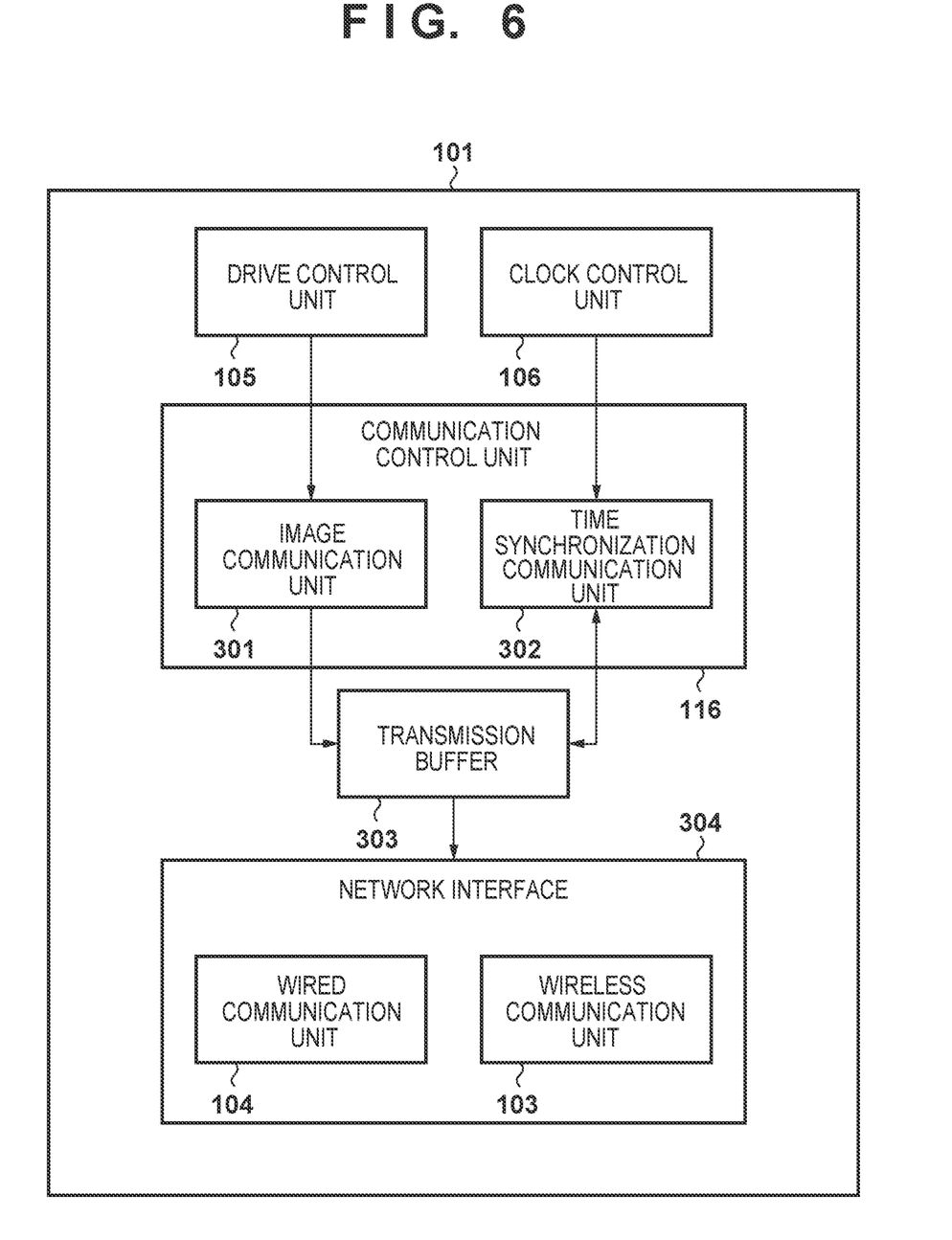
FIG. 6 is a diagram illustrating communication processing in a radiation imaging apparatus of a second embodiment.

FIG. 6 is a diagram illustrating communication processing in the radiation imaging apparatus in the second embodiment. In the radiation imaging apparatus 101, the communication control unit 116 includes an image communication unit 301 and a time synchronization communication unit 302. The image communication unit 301 acquires image data from a drive control unit 105, performs processing for generating an image data packet 401 and the like, and transmits the resulting packets to the transmission buffer 303. Also, the time synchronization communication unit 302 acquires time information from the clock control unit 106, performs processing for generating a time synchronization packet 402 and the like, and transmits the resulting packets to the transmission buffer 303.

The transmission buffer 303 temporarily stores the packets (the image data packet 401 and the time synchronization packet 402) received from the communication control unit 116, and transmits the packets to a network interface 304.

Figure 7:
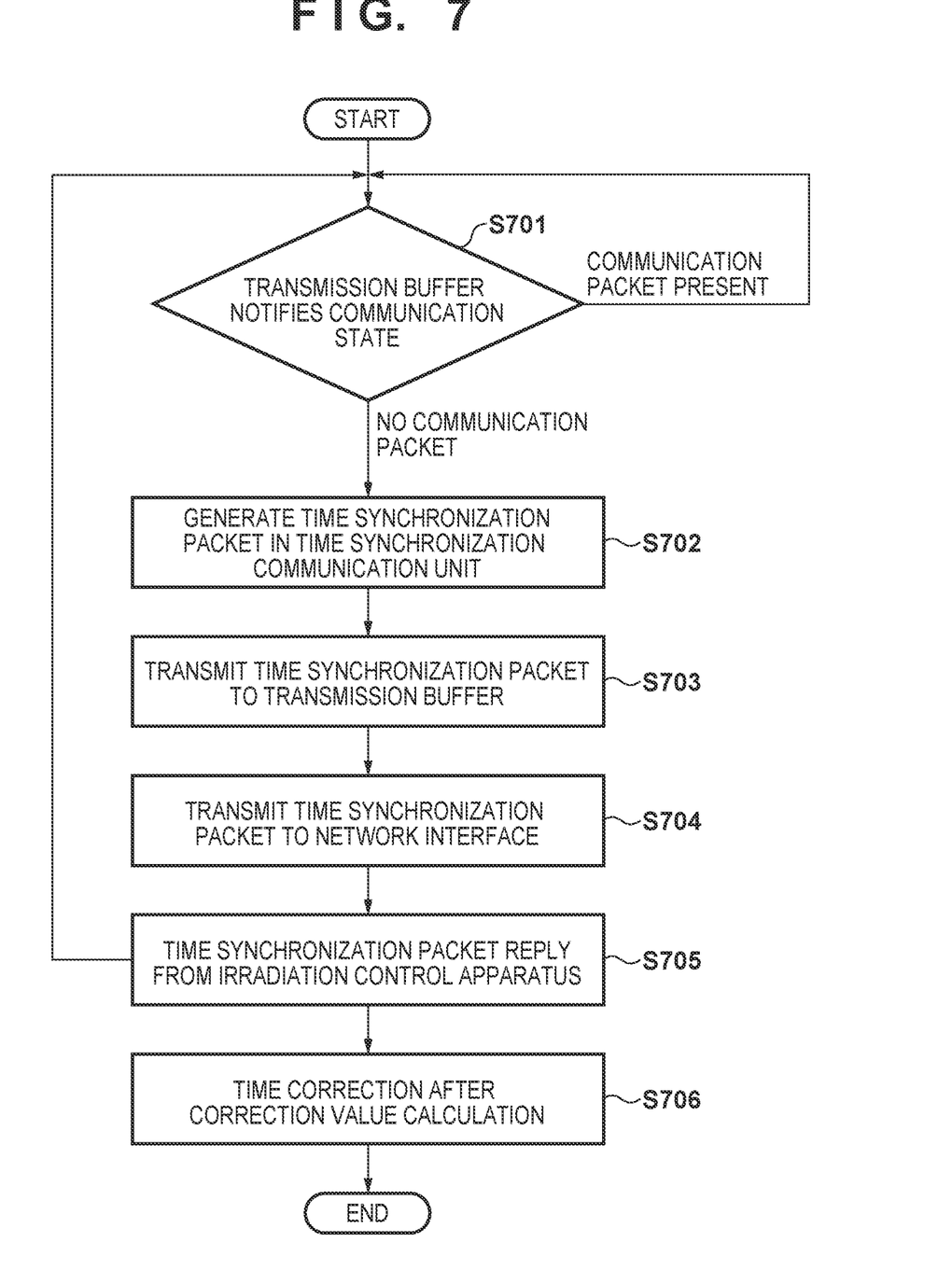
FIG. 7 is a diagram illustrating the flow of processing for transmitting a time synchronization packet in the second embodiment.

FIG. 7 is a diagram illustrating the flow of time synchronization packet transmission processing in the second embodiment.

In step S701, the transmission buffer 303 notifies the time synchronization communication unit 302 of a communication state with the image communication unit 301. For example, the transmission buffer 303 notifies the time synchronization communication unit 302 as to whether the transmission buffer 303 includes the image data packet 401. The transmission buffer 303 checks the communication state of the transmission buffer 303 in a certain cycle and notifies the time synchronization communication unit 302 of the state.

If the transmission buffer 303 stores the image data packet 401, the processing returns to step S701, the transmission buffer 303 checks the communication state of the transmission buffer 303 in a certain cycle and notifies the time synchronization communication unit 302 of the state. The transmission buffer 303 makes a notification regarding the communication state until the image data packet 401 is not included in the transmission buffer 303.

When, in step S701, it is determined that the transmission buffer 303 does not include the image data packet 401, the processing proceeds to step S702, the time synchronization communication unit 302 generates the time synchronization packet 402 in step S702, and the time synchronization communication unit 302 transmits the time synchronization packet 402 to the transmission buffer 303 in step S703.

In step S704, the transmission buffer 303 stores the time synchronization packet 402, and transmits the time synchronization packet 402 to the network interface 304. Then, the time synchronization packet 402 (time synchronization transmission information 200 (FIG. 2)) is transmitted from the network interface 304 to the irradiation control apparatus 120. When the time synchronization packet 402 is transmitted, the time when the time synchronization packet 402 is transmitted is stored in the radiation imaging apparatus 101 as an inquiry transmission time (FIG. 2).

In step S705, the irradiation control apparatus 120 makes a reply to the time synchronization packet 402 (time synchronization transmission information 200). The irradiation control apparatus 120 that has received the time synchronization transmission message 200 transmits a time synchronization reply message (time synchronization reply information 201) to the radiation imaging apparatus 101.

In step S706, the clock control unit 106 of the radiation imaging apparatus 101 calculates the correction value and performs time correction.

The radiation imaging apparatus 101 performs time average calculation based on a time when the time synchronization reply message (time synchronization reply information 201) transmitted from the irradiation control apparatus 120 is received (reply reception time) and the inquiry transmission time stored in step S704, and acquires an estimated reply time.

Then, the time information of the clock control unit 106 is corrected based on a time difference calculated using a difference between the estimated reply time in the clock control unit 106 of the radiation imaging apparatus 101 and the reply transmission time stored in the reply message (time synchronization reply information 201). Accordingly, the radiation imaging apparatus 101 and the irradiation control apparatus 120 enter a no-time-lag state (time synchronization state).

The radiation imaging apparatus 101 performs time average calculation based on a time when the time synchronization reply message (time synchronization reply information 201) transmitted from the irradiation control apparatus 120 is received (reply reception time) and the inquiry transmission time stored in step S704, and acquires an estimated reply time. Then, the radiation imaging apparatus 101 corrects the time information of the clock control unit 106 based on a difference time period (time difference) between the estimated reply time and the inquiry transmission time in the clock control unit 106 of the radiation imaging apparatus 101. Note that it is also possible to calculate a correction value for a time by repeating the processing flow from step S701 to step S705 a plurality of times so as to statistically process the time difference acquired through a plurality of instances of processing.

According to the present embodiment, the time synchronization communication unit 302 is capable of acquiring the communication state of an image data packet from the image communication unit 301 to the transmission buffer 303 by checking the state of the image data packet stored in the transmission buffer 303, and the time synchronization communication unit 302 is capable of controlling a time synchronization packet communication timing based on the information acquired from the transmission buffer 303 such that overlapping between the time synchronization packet transmission timing and the image data packet communication period is avoided. Accordingly, it is possible to prevent the time synchronization packet from remaining in the transmission buffer and being delayed.

According to the present embodiment, it is possible to provide a radiation imaging technique capable of easily performing time synchronization with higher accuracy and performing radiation imaging. Even if image data is transferred while a moving image is being captured, a time synchronization packet communication timing is controlled so as to avoid overlapping with an image data packet communication period, and an error in the time information is corrected between the radiation imaging apparatus 101 and the irradiation control apparatus 120, and thus it is possible to easily perform time synchronization with higher accuracy and perform radiation imaging under highly accurate time synchronization.

Other Embodiments

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-025353, filed Feb. 15, 2018, which is hereby incorporated by reference herein in its entirety.

What is claimed is:

1. A radiation imaging apparatus comprising:
a detection unit configured to detect emitted radiation and output radiation image data;
a clock control unit that has an internal clock and is configured to control a timing at which the detection unit is driven, based on time information of the internal clock; and
a communication unit configured to transmit and receive data through a network,
wherein the communication unit, transmits the time information to a control apparatus that is connected through the network if a communication traffic of the radiation image data is at a threshold or less, and
the clock control unit corrects the time information of the internal clock using time information that is a reply from the control apparatus to the time information.

2. The radiation imaging apparatus according to claim 1, further comprising:
an image communication unit configured to generate an image data packet from the radiation image data and transmit the generated image data packet to a transmission buffer; and
a time synchronization communication unit configured to acquire the time information from the clock control unit, generate a time synchronization packet, and transmit the generated time synchronization packet to the transmission buffer.

3. The radiation imaging apparatus according to claim 2, wherein, it is determined that the communication traffic in the communication unit exceeds a threshold and the time synchronization communication unit does not generate the time synchronization packet if the image data is stored in the transmission buffer.

4. The radiation imaging apparatus according to claim 2, wherein it is determined that the communication traffic in the communication unit is at a threshold or less, and the time synchronization communication unit generates the time synchronization packet if the image data is stored in the transmission buffer.

5. The radiation imaging apparatus according to claim 2, wherein the time synchronization communication unit makes an inquiry about an image communication schedule to the image communication unit, and
the time synchronization communication unit controls generation of the time synchronization packet based on the image communication schedule.

6. The radiation imaging apparatus according to claim 5, wherein the time synchronization communication unit determines, whether or not a time period from when communication of an image data packet ends to when communication of the next image data packet starts includes a gap time period in which the time synchronization packet can be transmitted to the transmission buffer based on the image communication schedule, and
controls generation of the time synchronization packet based on a result of the determination.

7. The radiation imaging apparatus according to claim 6, wherein, the time synchronization communication unit generates the time synchronization packet based on the result of the determination if the time period includes the gap time period.

8. The radiation imaging apparatus according to claim 2, wherein the clock control unit estimates an estimated reply time when the control apparatus replies with time synchronization reply information, based on a time when the time synchronization packet is transmitted and a reply reception time when the time synchronization reply information for the time synchronization packet is received from the control apparatus.

9. The radiation imaging apparatus according to claim 8, wherein a reply transmission time when the control apparatus has transmitted the time synchronization reply information is stored in the time synchronization reply information.

10. The radiation imaging apparatus according to claim 9, wherein the clock control unit obtains a correction value for a time from a difference time between the estimated reply time and the reply transmission time, and corrects the time information of the internal clock according to the correction value.

11. A radiation imaging system, comprising a radiation imaging apparatus and a control apparatus configured to control the radiation imaging apparatus, the radiation imaging apparatus comprising:
  a detection unit configured to detect emitted radiation and output radiation image data;
  a clock control unit that has an internal clock and is configured to control a timing at which the detection unit is driven, based on time information of the internal clock; and
  a communication unit configured to transmit and receive data through a network, wherein the communication unit transmits the time information to the control apparatus that is connected through the network if a communication traffic of the radiation image data is at a threshold or less, and the clock control unit corrects the time information of the internal clock using time information that is a reply from the control apparatus to the time information.

12. A method for controlling a radiation imaging system including a radiation imaging apparatus and a control apparatus configured to control the radiation imaging apparatus, the method comprising:
  detecting emitted radiation and outputting radiation image data using a detection unit;
  in a clock control unit that has an internal clock, controlling a timing at which the detection unit is driven, based on time information of the internal clock;
  a communication unit transmitting the time information to the control apparatus that is connected through a network if a communication traffic of the radiation image data is at a threshold or less, and
  correcting the time information of the internal clock using time information that is a reply from the control apparatus to the time information.

* * * * *